United States Patent
Shi et al.

(10) Patent No.: US 10,271,733 B2
(45) Date of Patent: Apr. 30, 2019

(54) PHOTO-ACOUSTIC SIGNAL ENHANCEMENT WITH MICROBUBBLE-BASED CONTRAST AGENTS

(75) Inventors: William Tao Shi, Briarcliff Manor, NY (US); Ladislav Jankovic, Fishkill, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 478 days.

(21) Appl. No.: 13/995,711

(22) PCT Filed: Dec. 12, 2011

(86) PCT No.: PCT/IB2011/055617
§ 371 (c)(1),
(2), (4) Date: Jun. 19, 2013

(87) PCT Pub. No.: WO2012/085751
PCT Pub. Date: Jun. 28, 2012

(65) Prior Publication Data
US 2013/0281848 A1 Oct. 24, 2013

Related U.S. Application Data

(60) Provisional application No. 61/425,808, filed on Dec. 22, 2010.

(51) Int. Cl.
*A61B 5/00* (2006.01)
*A61B 8/00* (2006.01)
(Continued)

(52) U.S. Cl.
CPC ............ *A61B 5/0095* (2013.01); *A61B 8/481* (2013.01); *A61K 49/223* (2013.01); *A61B 8/0833* (2013.01); *A61B 8/0883* (2013.01); *A61B 8/4483* (2013.01)

(58) Field of Classification Search
None
See application file for complete search history.

(56) References Cited

U.S. PATENT DOCUMENTS 5,420,579 A * 5/1995 Urbas et al. ............... 340/10.34
5,977,538 A 11/1999 Unger
(Continued)

FOREIGN PATENT DOCUMENTS

| WO | 2009057021 A2 | 5/2009 |
| WO | 2010020939 A2 | 2/2010 |
| WO | 2011045734 A1 | 4/2011 |

OTHER PUBLICATIONS

Kim, Chulhong et al. "Multifunctional Microbubbles and Nanobubbles for Photoacoustic and Ultrasound Imaging", Journal of Biomedical Optics, vol. 15, No. 1, Jan. 2010.
(Continued)

*Primary Examiner* — Thomas J Hong
*Assistant Examiner* — Marjan Saboktakin

(57) ABSTRACT

Bubbles (118-122) are utilized in some embodiments as part of a photoacoustic contrast agent (162) and, in some embodiments, to localize one or more locations (126-38) of a source of acoustic energy. The bubbles, such as microbubbles, can be used in proximity of nanoparticles of a first photoacoustic contrast agent, thereby affording a second photoacoustic contrast agent. The bubbles can intercept and re-radiate acoustic energy emitted by light-based activation of the first photoacoustic contrast agent in the immediate vicinity of the bubbles. As a further option, if the nanoparticles permeate further to tissue structures but remain in close enough proximity, their positions can be triangulated by the nearby bubbles, based on direction (144-148) and time delays (150-160) of ultrasound received by a transducer array.

5 Claims, 2 Drawing Sheets

(51) Int. Cl.
*A61B 8/08* (2006.01)
*A61K 49/22* (2006.01)

(56) References Cited

U.S. PATENT DOCUMENTS

| | | | |
|---|---|---|---|
| 6,662,040 B1 | 12/2003 | Henrichs | |
| 2004/0040379 A1 | 3/2004 | O'Donnell | |
| 2008/0045865 A1* | 2/2008 | Kislev | 601/3 |
| 2009/0149761 A1* | 6/2009 | Zou et al. | 600/476 |
| 2009/0156932 A1 | 6/2009 | Zharov | |
| 2010/0191109 A1 | 7/2010 | Fukutani | |
| 2010/0285518 A1* | 11/2010 | Viator | G01N 21/1702 |
| | | | 435/29 |

OTHER PUBLICATIONS

Wilson, Katheryne E. et al "Remotely Triggered Contrast NanoAgent for Ultrasound and Photoacoustic Imaging" 2010 IEEE Int'l Ultrasonics Symposium Proceedings, pp. 1003-1006.

Liao, Ai-Ho et al "An Imaging/Therapeutic Molecular Probe for Ultrasound and Photoacoustic Dual Modality System", Ultrasonics Symposium, 2010 IEEE.

Alippi, A. et al "Photoacoustic Cell for Ultrasound Contrast gent Characterization" AIP Review of Scientific Instruments, 2010.

Qu, Min et al "Magneto-Photo-Acoustic Imaging using Dual-Contrast Agent", 2010 IEEE Int'l Ultrasonics Symposium, pp. 511-514.

* cited by examiner

PHOTO-ACOUSTIC SIGNAL ENHANCEMENT WITH MICROBUBBLE-BASED CONTRAST AGENTS

FIELD OF THE INVENTION

The present invention is directed to the use of bubbles and, more particularly, to imaging through the use of bubbles.

BACKGROUND OF THE INVENTION

Photoacoustics is an emerging field within medical imaging. As photoacoustics relies on detection of the acoustic waves generated via optical absorption and the consequent heating/expansion process, the technology is closely tied to ultrasound. Typically, an intensity modulated light source, or short pulse source (i.e., laser), is used as the excitation source. The light is typically shined at the tissue surface, but can also be delivered from inside by means of minimally invasive delivery systems (e.g., endoscope, catheter, light-delivery needle). It penetrates the tissue predominantly via light scattering, thus illuminating a large volume. The light gets absorbed by blood/tissue chromophores, or non-targeted and targeted exogenous contrast agents such as optical dyes or nanoparticles configured for this purpose. The absorption, and consequent expansion, produces the acoustic wave, i.e., ultrasound or acoustic signal. The blood vessels (with different sizes and densities within a tumor, as well as different blood oxygenation level) and the surrounding tissue differ as to their light absorption. The resulting difference in the optically generated ultrasound produced provides contrast used in imaging. The technique's popularity is seen to be growing rapidly within the research community, focusing around some preclinical work such as whole body small animal imaging and monitoring pharmacokinetics, and clinical applications in oncology such as for breast or prostate cancer.

However, commonly-assigned International Publication Number WO 2009/057021 to Wang et al., (hereinafter "Wang"), entitled "Photoacoustic Imaging Contrast Agent and System for Converting Optical Energy to In-Band Acoustic Emission", which is incorporated herein by reference in its entirety, notes, and illustrates therein by FIGS. 1(a), 1(b), 2(a), 2(b), that photoacoustic (PA) signals generated by irradiating, with short laser pulses, a point absorber such as a PA contrast agent particle, are broadband, and only a fraction of the PA signal energy falls within the receive frequency range of a regular medical ultrasound transducer. A largely predominant portion of the energy falls outside the range, i.e., into a higher frequency range.

To address this, Wang places microbubbles and/or nanobubbles in close proximity of the PA contrast agent.

In particular, each nanoparticle in Wang incorporates evaporating material and light-absorbing material. When the light-absorbing material is excited or "activated" by irradiation, it evaporates its evaporating material to thereby create an attached bubble.

Advantageously, the system can be tuned so that the bubbles re-radiate the energy principally within the receive frequency range of a regular medical ultrasound transducer. The energy re-radiated has been amplified, and has spread out in all directions, including in the direction of an ultrasound transducer.

The nanoparticles, before activation, are small enough to cross the boundary between the vasculature and lymphatic system. Accordingly, permeability can be measured. Also as a consequence, more anatomy can be imaged.

Material from which a bubble is formed, and the light-absorbing material that causes formation of the bubble, are combined in a particle, or droplet, in ways that differ according to the embodiment, thereby collectively offering a range of bubble size, and of bubble longevity over repeated expansions.

SUMMARY OF THE INVENTION

The present inventors have observed that, in addition to the above-discussed bandwidth mismatch problem, conventional PA imaging of an object, such as a cyst, a heart or a lymph node, primarily identifies merely the tissue boundaries, as the technique relies on differential optical absorption. The differential absorption creates respectively differential expansion in the tissue. The ultrasound generated at the boundary, by the expansion, will tend to be less visible to the extent the boundary faces away from the ultrasound transducer. Accordingly, only the insonification-direction boundaries are clearly visible.

What is proposed herein is an extension of Wang and is directed to addressing one or more of the concerns described above.

As proposed herein, a bubble, as in Wang, is positioned in close proximity of a PA contrast agent such as a dye-based or nanostructured PA contrast agent, and likewise re-radiates acoustic energy omni-directionally. Accordingly, the above-noted angle dependence in imaging is analogously overcome, with the bubbles filling tissue structures so as to aid in their visualization, so that an ultrasound transducer can be utilized to more fully detect the structure based on the ultrasound received from the bubbles.

In addition, in the current proposal, the bubble is free floating and can be pre-made, affording more flexibility as to size and longevity. Yet, the bubble can still function to relay acoustic energy provided by nano-sized particles that have permeated to areas microbubbles are too big to reach. With regard to size, the scattering cross-section of a bubble is a few orders (up to $10^6$) greater than its geometrical cross-section, allowing contrast microbubbles closely surrounding a point PA source to effectively intercept the acoustic energy to be relayed.

In an aspect of the present invention, an imaging contrast agent includes bubbles and a first photoacoustic contrast agent separately free-floating from the bubbles. The imaging contrast agent serves as a second photoacoustic contrast agent.

In a related aspect, a second photoacoustic contrast agent includes bubbles and a first photoacoustic contrast agent in a non-activated state.

In another related aspect, a method includes positioning contrast agent for relaying acoustic energy received that was emitted by a source having a location for being imaged. The imaging is based on the relayed energy. A physical separation exists between the source and a bubble the agent comprises.

As a sub-aspect, the positioning comprises at least one of: a) injecting the agent into body tissue to mix with the source; and b) mixing the agent with the source externally.

In another sub-aspect, the source includes a photoacoustic contrast agent.

In a different sub-aspect, the source has multiple locations. The agent includes bubbles for imaging ones of the multiple locations.

In a further sub-aspect, the positioning includes controlling bubble concentration, to maximize contrast coverage and to minimize multiple scattering.

In a complementary sub-aspect, time delays, and directions, of ultrasound received from ones of the plural bubbles are used to localize at least a portion of the source.

As yet another sub-aspect, the agent serves as a composite contrast agent in that it further comprises a photoacoustic contrast agent.

In a still further sub-aspect, the composite contrast agent is configured for, due to proximity of the bubble to the photoacoustic contrast agent, serving as a second photoacoustic contrast agent.

In an alternative aspect, a method for forming, as a mixture, a second photoacoustic contrast agent includes joining, to mix, a first group with a second group. The second group includes bubbles. The first group includes particles of a first photoacoustic contrast agent.

In one sub-aspect, the joining is performed outside of a body of a subject to receive the mixture.

In another version, onset of the mixing occurs within a body of a subject.

A sub-aspect of the alternative aspect involves controlling, in real time under the guidance of bubble-specific ultrasound imaging, concentration of bubbles of the second photoacoustic contrast agent at an imaging site toward concurrent goals of contrast coverage and minimizing multiple scattering.

In a related version, a device is configured for localizing one or more locations of a source of acoustic energy. The energy is relayed by a contrast agent that includes a bubble. A physical separation exists between the source and the bubble. The device includes, or is connectable communicatively with, an apparatus for receiving the relayed energy. The localizing is based on the relayed energy received.

In a sub-version, the apparatus the device comprises includes an ultrasound transducer array comprising a spatial distribution of elements and serving as an imaging array.

In an alternative sub-version, the device is implemented as one or more integrated circuits for being communicatively connected to the apparatus.

In yet another version, a device is configured for using time delays, and directions, of ultrasound received from a plurality of bubbles to localize a source of acoustic energy. The bubbles relay the energy as the ultrasound to be received. The device includes, or is connectable communicatively with, an apparatus for receiving the relayed energy. The localizing is based on the relayed energy received.

What is proposed herein is realizable as methods, compositions of matter for carrying out the methods, devices for performing the methods, computer programs for carrying out the functionality of the devices, signals for conveying the functionality, and/or methods for generating the signals. A method for generating a signal comprises varying an electrical current applied to at least one of: a) a wire input to said device; and b) an antenna for transmitting, so as to, by the varying, generate the signal.

Details of the novel, photoacoustic contrast agent technology are set forth further below, with the aid of the following drawings.

DETAILED DESCRIPTION OF EMBODIMENTS

Figure 1:
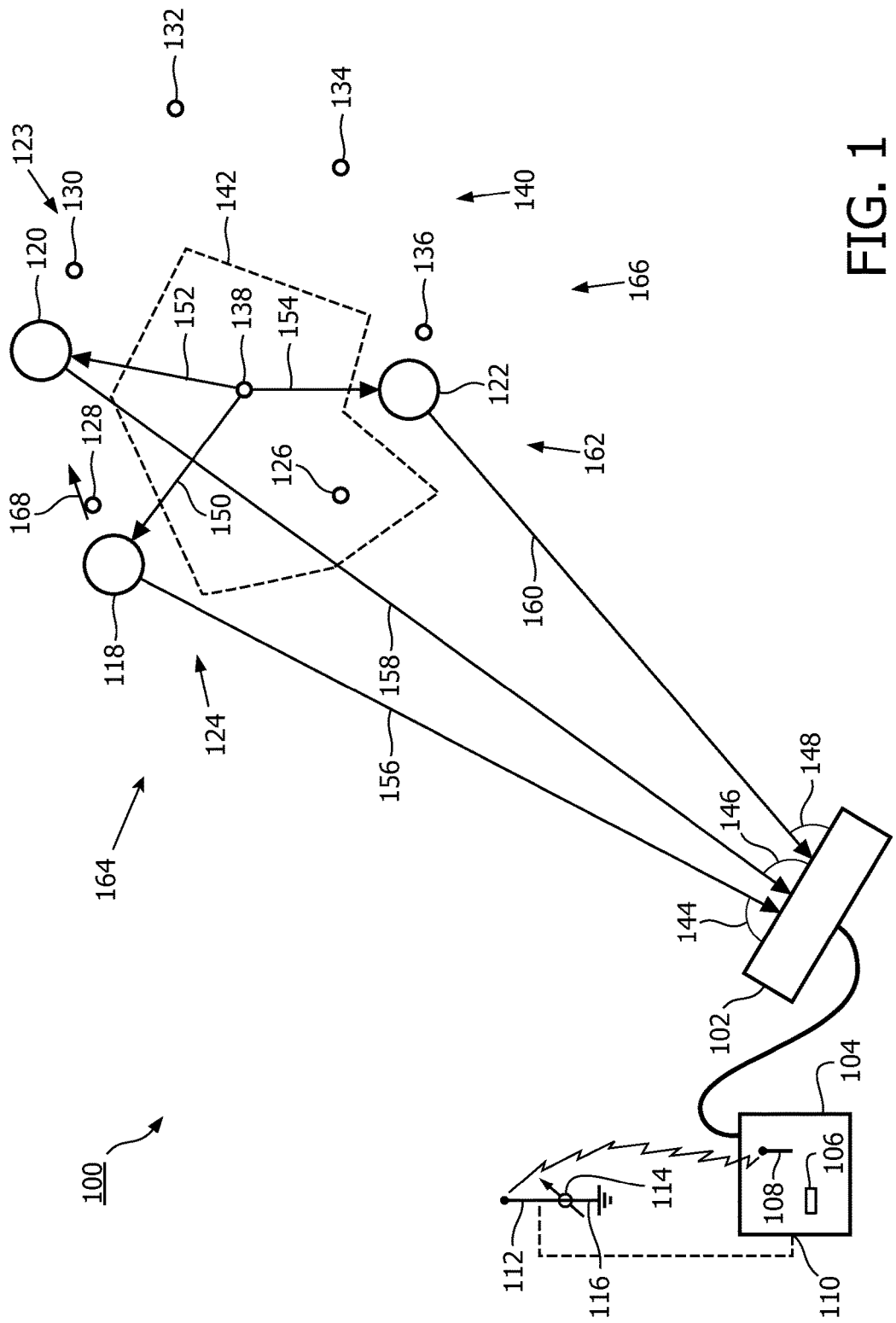
FIG. 1 is a schematic and conceptual diagram of an exemplary photoacoustic system.

A photoacoustic (PA) system 100, as shown in FIG. 1 by way of illustrative and non-limitative example, includes, as an imaging array, an ultrasound transducer array 102 connected by a cable to a control unit 104. The transducer array 102 comprises a spatial distribution of transducer elements (not shown). The control unit 104 can include, as control electronics, one or more integrated circuits (ICs) as a controller 106, and optionally, for receiving control information, an antenna 108 and/or a wire input 110. The controller 106 is connectable communicatively with the transducer array 102, as by the cable or a wireless connection. The antenna 108 receives control information transmitted by a source antenna 112. The control information is formed by varying 114 an electrical current of an electrical circuit 116. The control information, if fed to the control unit 104, may also be conveyed by a wired connection to the wire input 110.

Microbubbles 118, 120, 122, which can serve as an ultrasound (US) contrast agent 123, are shown in FIG. 1 free floating in body tissue 124. The body tissue 124 can be that of a medical patient or, more generally, that of a human or animal subject or of a specimen.

Microbubbles, having diameters of from 1 to 5 microns on average, are often confined to the vasculature, although some are small enough to pass into the lymphatic system. Nanoparticles 126, 128, 130, 132, 134, 136, 138, which comprise a PA contrast agent or "acoustic energy source" 140, are small enough to make the passage. The nanoparticles 126-138 may be of any known and suitable type serving as a PA contrast agent, e.g., gold or carbon nano-rods or nano-spheres.

The nanoparticle 126 is shown within a tissue structure 142 that the microbubbles 118 may be too big to reach.

The microbubble 118 is positioned at a physical separation from, but is close enough to, the nanoparticle 128 that the short PA pulse travels merely a short distance before energizing the microbubble. Thus, attenuation loss at this proximity is small. Also, the PA pulse is broadband, and relatively little acoustic attenuation loss occurs in biological tissue with respect to comparatively lower acoustic frequencies to be relayed. Accordingly, the microbubble 118 intercepts and re-radiates the acoustic energy, acting as a non-linear acoustic energy converter and as an acoustic signal amplifier.

The same can be said for the other microbubbles 120, 122 shown in FIG. 1, and for their nearby nanoparticles 130, 136, respectively, which are other portions of the source 140 of acoustic energy, that energy arising due to the application of the current laser pulse. At least a portion of the source 140 is to be imaged.

Pulse-echo imaging of the microbubble 118-122 need not rely on a pulse from the ultrasound transducer array 102. Instead, in the case of photoacoustics, the original pulse is from the laser (not shown) which may be repeatedly emitting laser pulses.

The pulse-echo imaging used here, unlike that already used in photoacoustics, is based on ultrasound relayed (scattered or reflected) from bubbles, and proceeds as follows. The laser pulse causes a pulse of acoustic energy from the nearby nanoparticle 128, 130, 136 which, in turn, causes oscillation of the nearby bubble 118-122. The oscillation transmits ultrasound that is received by the transducer array 102. The original laser pulse travels with the speed of light which is much faster than acoustic wave propagation speed. It is also assumed that the nanoparticle 128, 130, 136 is negligibly close to its respective microbubble 118-122. Thus, time delay or "time-of-flight" (TOF) between the laser pulse and a particular element of the transducer array 102 can be visualized as the magnitude of a radius to a partial spherical surface concentric with the element, with the microbubble 118-122 located somewhere on the spherical surface. Multiple ones, or all, of the elements can have their own spherical surfaces for that particular microbubble 118-122. Conversely, each of the microbubbles 118-122 has its own respective set of spherical surfaces, each surface corresponding to its own element. TOF from microbubbles at different distances from a given element can be distinguished by an increase, during the reception time window, in received acoustic pressure magnitude. Two spherical surfaces of respective transducer elements intersect to form a curved line, and a third one may intersect with the line to form a point. For each point formed from the above-noted spherical surfaces, an increment of "light" is assigned. Some points in the body tissue, or "volume of interest" (VOI) 124, therefore have light, and, incrementally, some more than others. The points with the most light are geometrically localized in the VOI as the positions of the microbubbles 118-122. In summary, the microbubble 118, 120 or 122 relays (scatters/reflects) ultrasound pulses from a nearby PA source (as in PA imaging) at the location of the nanoparticle 128, 130 or 136, respectively, the locations of the microbubbles 118-122 becoming known according to nearby nanoparticles 128, 130 and 136 that are very close to the respective microbubbles.

Later-arriving radiofrequency data from the each of the microbubbles 118-122 may be distinguished based again on an increase of the observed acoustic pressure magnitude during the receive time window. The arriving data can be indicative of the nanoparticle 138, for those situations in which the microbubbles are not located immediately near the nanoparticle, i.e., the relatively larger microbubbles are unable to reach certain tissue structures. From the already-localized microbubbles 118-122 partial spherical surfaces whose radius respectively reflects the additional TOF can be used to likewise triangulate and thereby localize the "remote" nanoparticle 138. Accordingly, angles 144, 146, 148 and respective physical separations, or equivalently, TOFs 150, 152, 154 are utilized to localize the remote nanoparticle 138. The angles 144-148 represent the directions in which acoustic energy emitted by the PA contrast agent, or "source", 140 is relayed by the microbubbles 118-122 to the respective elements of the transducer array 102. Indirectly, the previously-determined TOFs 156, 158, 160 to the microbubbles 118-122 are also used in the localization. The TOFs 156-160 are shown as corresponding to respective elements of the transducer array 102, but the same analysis can be performed over multiple elements.

It should be pointed out that, because the distance between the microbubble 118 (or 120 or 122) and the nanoparticle 138 is much less than the distance between the microbubble 118 (or 120 or 122) and the array 102, the microbubbles 118-122 still act as acoustic signal enhancers for the nanoparticle 138 of the source 140.

Note that the microbubbles 118-122 can also relay (scatter/reflect) ultrasound pulses transmitted from the array 102 (as in ultrasound imaging). Thus, the locations of the microbubbles 118-122 can be determined with, e.g., microbubble-specific ultrasound contrast imaging. The localization of microbubbles as in ultrasound contrast imaging, in turn, makes it much more convenient and accurate to determine the locations of nanoparticles (such as the nanoparticle 138) as in the PA imaging. In addition, a higher frame rate for ultrasound imaging, if required, can be achieved using fewer broad beams (one very broad beam in the limiting case) for transmitted ultrasound pulse sequences.

Also, although three microbubbles 118-122 are used in the example, more may be used in the calculation if more have data to contribute. Additionally, other nanoparticles 126 are disposed at locations of the PA contrast agent 140 for being imaged. Thus, these other nanoparticles 126 can likewise be localized to fill out the imaging of the microbubble-inaccessible region.

Thus, the first PA contrast agent 140, even when in a non-activated state, constitutes, when combined with the microbubbles 118-122, a second PA contrast agent 162. Here, the first PA contrast agent 140 is separately free-floating from the microbubbles 118-122, even when the two are joined by mixing them together.

Contrast coverage 164 at the site 166 to be imaged extends beyond the tissue structure 142 to include the microbubbles 118-122 in the example shown in FIG. 1.

Multiple scattering 168 of acoustic energy between microbubbles 118, 120 as shown in FIG. 1, will distort the imaging. The multiple scattering 168 is to be minimized by decreasing bubble concentration while maximizing the contrast coverage 164 by increasing the concentration.

Figure 2:
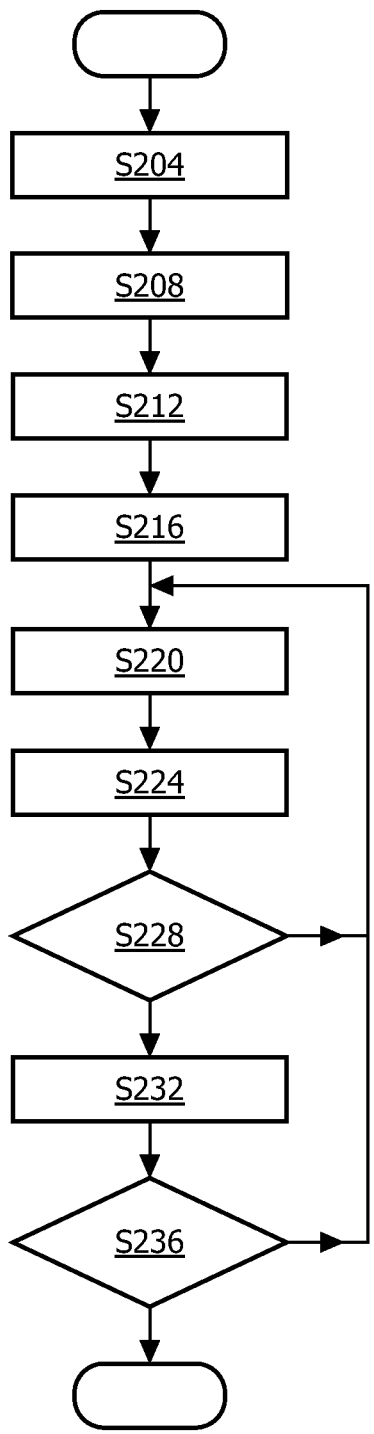
FIG. 2 is a flow chart which illustrates operation of the system in FIG. 1.

Operationally, and with reference to FIG. 2, a receive bandwidth for the medical ultrasound application is determined (step S204). Imaging deeper lesions, for example, will require a band of lower ultrasound frequencies at the expense of resolution. Conversely, interrogating shallower objects can be done with a bandwidth that includes higher frequencies. Since the resonance frequency of a bubble varies inversely with its size, a range of bubble sizes is then selected to come within the receive frequency range of the ultrasound transducer array 102 (step S208).

Mixing/administration of the US contrast agent 123 with the selected bubble sizes is performed (step S212).

There are a number of different possible ways this can be done.

The PA contrast agent or "first group" 140 can, e.g., in a non-activated state, be mixed with the US contrast agent or "second group" 123 to form the second PA contrast agent 162.

The mixing may be performed during, and/or just before, the clinical examination, although at this stage of the current example the mixing occurs just before the examination, and it can be performed internally, i.e., within the patient or subject, or externally. For example, the first group 140 and the second group 123, after being diluted, may fill two separate syringe pumps. The timing and rate of injection of each group, as by infusion by means of an intravenous catheter (IV), can be controlled by each pump independently. The output of the two pumps is mixed to form the PA contrast agent 162 and then infused either directly, or indirectly by means of a saline infusion line, into the patient. The infusion can occur before and/or during the imaging examination. Timing and dosage for each group 140, 123 can be independently controlled. The mixing has the effect of positioning the US contrast agent 123, by virtue of the consequent proximity of the microbubbles 118-122 to respective nanoparticles 126-138, for relaying acoustic energy received that was emitted by the source 140. The US contrast agent 123 remains so positioned after infusion.

Alternatively, the patient can be infused or injected with a combination of the two groups 140, 123 that was premixed substantially prior to the imaging examination. Here, too, the mixing positions the ultrasound contrast agent 123, by virtue of the consequent proximity of the microbubbles 118-122 to respective nanoparticles 126-138, for relaying acoustic energy received that was emitted by the source 140. Likewise, the US contrast agent remains so positioned after infusion.

It is also possible for one group 140, 123 to be infused systematically into the bloodstream while another group is directly injected into the object, e.g., lesion, so that the onset of mixing occurs internally.

As a further example, both groups 140, 123 are injected or infused directly into the object at the same time or at different times.

A patient, alternatively, could ingest both groups 140, 123 concurrently or separately in, for example, the case of intestinal imaging. Or, perhaps, the groups 140, 123 could be, as another example, injected, through the urethra, into the kidneys, of PA examination of the kidneys.

In any event, the mixing and/or the administration timing or rate may be performed so as to, with respect to the imaging site 166, maximize contrast coverage 164 while minimizing multiple scattering 168 between microbubbles 118-122.

The site 166 can be monitored by ultrasound contrast agent pulse-echo imaging to detect when the microbubbles 118-122 have filled the site sufficiently for the examination (step S216), at which point in time a laser pulse can be fired at the site (step S220). The acoustic energy thereby produced is relayed for reception by the ultrasound transducer array 102 (step S224).

The laser pulsing and reception steps S220, S224 can be done repeatedly to accumulate more data for analysis (step S228). Optionally, the laser pulsing step S220 may, at times, include the above-described microbubble-specific ultrasound contrast imaging as a technique alternative to PA imaging for localizing the microbubbles 118-122, the technique being performed to update the localization.

When the pulsing and reception steps S220, S224 are not to be repeated, such as at a pause to check results (step S228), or, alternatively, while they continue to be repeated, the user can make, in real time under imaging guidance, an adjustment to the mixing and/or administration timing or rate to more fully realize the concurrent goals of contrast coverage maximizing and multiple scattering minimizing (step S232). The imaging guidance can involve monitoring microbubble concentration that exists at the imaging site 166, by microbubble-specific ultrasound contrast imaging for example.

Then, if examination is to continue (step S236), processing returns to step S220; otherwise, if examination is not to continue, the procedure terminates.

Bubbles are utilized in some embodiments as part of a photoacoustic contrast agent and, in some embodiments, to localize one or more locations of a source of acoustic energy. The bubbles, such as microbubbles, can be used in proximity of nanoparticles of a first photoacoustic contrast agent, thereby affording a second photoacoustic contrast agent. The bubbles can intercept and re-radiate acoustic energy emitted by light-based activation of the first photoacoustic contrast agent in the immediate vicinity of the bubbles. As a further option, if the nanoparticles permeate further to tissue structures but remain in close enough proximity, their positions can be triangulated by the nearby bubbles, based on direction and time delays of ultrasound received by a transducer array.

Although methodology according to what is proposed herein can advantageously be applied in providing medical diagnosis for a human or animal subject, the intended scope of claim coverage is not so limited. More broadly, enhanced photoacoustic imaging, in vivo, in vitro or ex vivo is envisioned.

The proposed technology is directly applicable to cardiovascular imaging and oncology, which are the usual target application areas for PA imaging.

While the invention has been illustrated and described in detail in the drawings and foregoing description, such illustration and description are to be considered illustrative or exemplary and not restrictive; the invention is not limited to the disclosed embodiments.

For example, nano-bubbles may be used in place of microbubbles in any or all of what is proposed above.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A signal embodying the above-described inventive functionality of the device 100, and for conveying it to the device, is formable by appropriately varying an electrical current. The signal can arrive by a device input wire, or be transmitted wirelessly by an antenna.

A single processor or other unit may fulfill the functions of several items recited in the claims. The mere fact that certain measures are recited in mutually different dependent claims does not indicate that a combination of these measures cannot be used to advantage.

The invention claimed is:

1. A photoacoustic system for imaging contrast agents, the system comprising:
   an ultrasound imaging array configured to transmit ultrasound into a site within a patient tissue comprising a mixture of an ultrasound contrast agent and a photoacoustic contrast agent;
   a laser configured to generate a laser pulse to activate the photoacoustic contrast agent; and
   a computer operatively coupled to the ultrasound imaging array and the laser, the computer configured to:
   control the laser to generate the laser pulse so as to activate the photoacoustic contrast agent that is separately free-floating from the ultrasound contrast agent, wherein the activated photoacoustic contrast agent causes the ultrasound contrast agent to generate ultrasound;
   control the ultrasound imaging array to receive ultrasound transmitted from the ultrasound contrast agent;
   determine (1) time delays between the laser pulse and times when the ultrasound from the ultrasound contrast agent is received by the ultrasound imaging array and (2) angles in relation to a surface of the array that represent a direction in which the ultrasound transmitted from the ultrasound contrast agent impinges the array; and based on the time delays and the angles, triangulate a location of the photoacoustic contrast agent in the patient tissue.

2. The photoacoustic system of claim 1, wherein the computer comprises a controller configured to control at least one of the generation of the laser pulse and the operation of the ultrasound imaging array of the system.

3. The photoacoustic system of claim 1, further comprising a dispenser for delivering the ultrasound contrast agent and photoacoustic contrast agent to the patient.

4. The photoacoustic system of claim 3, wherein the dispenser is configured to deliver the ultrasound contrast agent and the photoacoustic contrast agent to the patient as a mixture.

5. The photoacoustic system of claim 1, wherein the computer is configured to control the laser to repeatedly transmit laser pulses, and wherein the computer is further configured to control the ultrasound imaging array to transmit ultrasound from the imaging array to the patient tissue intermittently with the laser pulses.

* * * * *